US007081161B2

(12) United States Patent
Genge et al.

(10) Patent No.: US 7,081,161 B2
(45) Date of Patent: *Jul. 25, 2006

(54) BIOCOMPATIBLE CEMENT CONTAINING REACTIVE CALCIUM PHOSPHATE NANOPARTICLES AND METHODS FOR MAKING AND USING CEMENT

(75) Inventors: Brian R. Genge, Columbia, SC (US); Licia Wu, Cayce, SC (US); Glenn R. Sauer, Fairfield, CT (US); Roy E. Wuthier, Columbia, SC (US); Ronald Genge, Watertown, WI (US)

(73) Assignee: University of South Carolina, Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/841,885

(22) Filed: May 7, 2004

(65) Prior Publication Data
US 2006/0118007 A1    Jun. 8, 2006

Related U.S. Application Data

(62) Division of application No. 09/978,601, filed on Oct. 16, 2001.

(60) Provisional application No. 60/239,980, filed on Oct. 16, 2000.

(51) Int. Cl.
C04B 12/02    (2006.01)
(52) U.S. Cl. ........................... 106/690; 106/35
(58) Field of Classification Search ................ 106/690, 106/35
See application file for complete search history.

(56) References Cited

U.S. PATENT DOCUMENTS 4,880,610 A    11/1989  Constantz ................. 423/305
5,034,059 A    7/1991   Constantz ................. 106/161
5,047,031 A    9/1991   Constantz ................. 606/77
5,053,212 A    10/1991  Constantz et al. .......... 423/305
5,129,905 A    7/1992   Constantz ................. 606/76
5,149,368 A    9/1992   Liu et al. ................. 424/602
5,336,264 A    8/1994   Constanz et al. ............ 623/16
5,455,231 A    10/1995  Constantz et al. .......... 514/21
5,496,399 A    3/1996   Ison et al. ................. 106/35
5,522,893 A    6/1996   Chow et al. ................ 623/11
5,525,148 A    6/1996   Chow et al. ................ 106/35
5,542,973 A    8/1996   Chow et al. ................ 106/35
5,545,254 A    8/1996   Chow et al. ................ 106/35
5,569,442 A    10/1996  Fulmer et al. ............. 423/311
5,571,493 A    11/1996  Fulmer et al. ............. 423/308
5,605,713 A    2/1997   Boltong .................... 427/2.1

(Continued)

FOREIGN PATENT DOCUMENTS

DE    19813614 A1    9/1999

(Continued)

OTHER PUBLICATIONS

K.E. Watons, et al., *The formation of hydroxyapatite-calcium polyacrylate composites*, J. of Materials Science in Medicine, 10:205-213 (1999).

*Primary Examiner*—Paul Marcantoni
(74) *Attorney, Agent, or Firm*—Nelson Mullins Riley & Scarborough, LLP

(57) ABSTRACT

A cement powder is disclosed that contains reactive tricalcium phosphate nanoparticles and other ingredients required to form a cementous material. Methods of making the reactive tricalcium phosphate nanoparticles, the cement powder, the cement paste, and cured cement are also provided, as are methods and articles for using the cement.

35 Claims, 7 Drawing Sheets

U.S. PATENT DOCUMENTS

| | | | |
|---|---|---|---|
| 5,683,496 A | 11/1997 | Ison et al. | 106/35 |
| 5,683,667 A | 11/1997 | Fulmer et al. | 423/311 |
| 5,695,729 A | 12/1997 | Chow et al. | 423/305 |
| 5,709,742 A | 1/1998 | Fulmer et al. | 106/690 |
| 5,820,632 A | 10/1998 | Constantz et al. | 623/16 |
| 5,885,540 A | 3/1999 | Fulmer et al. | 423/311 |
| 5,952,010 A | 9/1999 | Constantz | 424/602 |
| 5,954,867 A | 9/1999 | Chow et al. | 106/35 |
| 5,962,028 A | 10/1999 | Constantz | 424/602 |
| 5,976,234 A | 11/1999 | Chow et al. | 106/35 |
| 5,997,624 A | 12/1999 | Chow et al. | 106/35 |
| 6,002,065 A | 12/1999 | Constantz et al. | 623/16 |
| 6,005,162 A | 12/1999 | Constantz | 623/16 |
| 6,013,591 A | 1/2000 | Ying et al. | 501/1 |
| 6,027,742 A | 2/2000 | Lee et al. | 424/422 |
| 6,808,561 B1 * | 10/2004 | Genge et al. | 106/690 |

FOREIGN PATENT DOCUMENTS

| | | |
|---|---|---|
| GB | 2 156 824 A | 3/1985 |
| JP | 11267194 A | 10/1999 |
| WO | WO 99/49906 | 10/1999 |
| WO | WO 00/03747 A2 | 1/2000 |
| WO | WO 00/03747 A3 | 1/2000 |
| WO | WO 00/45867 A1 | 8/2000 |

* cited by examiner (a)

(b)

250 X

1000 X

US 7,081,161 B2

BIOCOMPATIBLE CEMENT CONTAINING REACTIVE CALCIUM PHOSPHATE NANOPARTICLES AND METHODS FOR MAKING AND USING CEMENT

CROSS REFERENCE TO RELATED PATENTS AND PATENT APPLICATIONS

The present application is a divisional of copending U.S. patent application Ser. No. 09/978,601, which was filed on Oct. 16, 2001, and which was a non-provisional of U.S. Provisional Patent Application Ser. No. 60/239,980, filed Oct. 16, 2000, both of which applications are hereby incorporated herein by reference in their entirety.

Work leading to this invention was supported, at least in part, by federal research grant no. N00014-97-1-0806, Department of Defense, Office of Naval Research, and the federal government may retain some rights in the invention.

BACKGROUND OF THE INVENTION (1) Field of the Invention

The present invention relates to the production and use of cement-type materials that can be used in biological applications, and more particularly to the production and use of calcium-phosphate cement-type materials that can be used in biological applications.

(2) Description of the Related Art

To date, a wide variety of implant materials have been used to repair, restore, and augment bone. The most commonly used implants include autologous bone, synthetic polymers, and inert metals. Protocols using these materials have significant disadvantages that can include patient pain, risk of infection during operations, lack of biocompatibility, cost, and the risk that the inserted hardware can further damage the bone. Therefore, a major goal of biomaterial scientists and plastic and reconstructive orthopedic surgeons has been to develop novel bone substitutes that can be used as alternatives to these conventional techniques for skeletal repair. Ideally, treatment of such injuries as bone fractures, for example, should achieve anatomical reduction of the fracture, avoid unnecessary tissue damage, and provide temporary stability until healing occurs.

To this end, interest in the early 1980's focused on the use of hydroxyapatite $[Ca_{10}(PO_4)_6(OH)_2]$ to augment skeletal defects and for use as a coating on prosthetic implants. Sintered hydroxyapatite is a biomaterial that has attracted much interest as a substitute for injured bone and teeth due to its chemical and crystallographic similarities to the principal inorganic constituent of these hard tissues. However, sintered, preformed hydroxyapatite prosthetic devices have several disadvantages that include being difficult for the surgeon to physically shape and install, having insufficient strength to support heavy loads, and are only very slowly resorbed by the host—typically at a rate of less than 1% per year.

Bone cements, such as cements based on polymethylmethacrylate (PMMA) offer certain advantages in avoiding the use of solid implants, but also have several disadvantages. Methacrylates and methacrylic acid are known irritants to living tissues, and when PMMA-based cements are cured in vivo, free-radicals are generated, which can damage surrounding tissues. Moreover, the polymerization reaction for these materials is highly exothermic, and the heat evolved during curing can damage tissues.

More recently, calcium and phosphate-based bone cements (CPCs) and pastes have been the subject of much attention as potentially superior bone substitutes because they show excellent biocompatibility and appear to be resorbed. CPCs are rapidly emerging as third generation bone substitutes and could potentially positively impact many diverse areas of orthopedic, cranialfacial, and reconstructive surgery. However, current calcium phosphate-based bone cements appear to lack sufficient compressive strength and are therefore only potentially suitable for use in treating injuries to non-weight-bearing bones such as wrist fractures and in cranial/facial augmentation surgeries.

Accordingly, it would be useful to provide a material that could be used as a bone cement that was non-toxic and biocompatible with the tissue surrounding its site of use. It would also be useful if such material was self-setting—needing no irritating initiator or accelerator to promote curing, and also that the curing itself did not generate free-radicals or heat sufficient to harm surrounding tissues. It would also be useful if such material could be provided in a physical form that could be injected, flowed or applied to the site of action in a manner that would permit a minimum of invasive surgery and would allow the cement to intimately contact the parts to be joined. It would also be useful if such material could cure quickly, and to develop a high compressive strength upon curing. It would also be useful if such material was bioabsorbable by the host.

SUMMARY OF THE INVENTION

Briefly, therefore, the present invention is directed to a novel cement powder comprising reactive tricalcium phosphate nanoparticles and other ingredients required to form a cementous material.

The present invention is also directed to a novel cement paste comprising a lubricating liquid which is intermixed with a cement powder that includes reactive tricalcium phosphate nanoparticles and other ingredients required to form a cementous material.

The present invention is also directed to a novel biocompatible cured cement comprising the cured form of a cement paste comprising a lubricating liquid which is intermixed with a cement powder that includes reactive tricalcium phosphate nanoparticles and other ingredients required to form a cementous material.

The present invention is also directed to a novel method of making a cement powder containing reactive tricalcium phosphate nanoparticles, the method comprising forming the reactive tricalcium phosphate nanoparticles by precipitation from solution; and intermixing the nanoparticles with other ingredients required to form a cementous material.

The present invention is also directed to a novel method of making a cement paste containing reactive tricalcium phosphate nanoparticles, the method comprising intermixing a lubricating liquid with a cement powder that includes reactive tricalcium phosphate nanoparticles and other ingredients required to form a cementous material.

The present invention is also directed to a novel method of binding articles together comprising: providing a cement paste comprising a lubricating liquid which is intermixed with a cement powder that includes reactive tricalcium phosphate nanoparticles and other ingredients required to form a cementous material; placing the cement paste at an interface of the articles to be bound together; and curing the cement paste to form a bond between the articles.

The present invention is also directed to a novel article that is formed from a biocompatible cured cement comprising the cured form of a cement paste comprising a lubricating liquid which is intermixed with a cement powder that includes reactive tricalcium phosphate nanoparticles and other ingredients required to form a cementous material.

The present invention is also directed to a novel method of storing a calcium-phosphate-type cement paste comprising cooling the cement paste to a temperature that is sufficiently low to preserve the flowability and curing properties of the cement paste so that when the cement paste is reheated to ambient temperature these properties are substantially returned to the state of the paste prior to cooling.

The present invention is also directed to novel reactive tricalcium phosphate nanoparticles that have been produced by precipitation from a sulfate-containing solution which is free of carbonate and which has a calcium:phosphate ratio of less than about 1.5:1.

Among the several advantages found to be achieved by the present invention, therefore, may be noted the provision of a material that could be used as a bone cement that was non-toxic and biocompatible with the tissue surrounding its site of use, the provision of such a material that was self-setting—needing no irritating initiator or accelerator to promote curing, and also that the curing itself did not generate free-radicals or heat sufficient to harm surrounding tissues, the provision of such a material in a physical form that could be injected, flowed or applied to the site of action in a manner that would permit a minimum of invasive surgery and would allow the cement to intimately contact the parts to be joined, the provision of such a material that could cure quickly, and develop a high compressive strength upon curing, the provision of such material that was bioabsorbable by the host, and the provision of methods to make and use such materials.

DETAILED DESCRIPTION OF THE PREFERRED EMBODIMENTS

Figure 1:
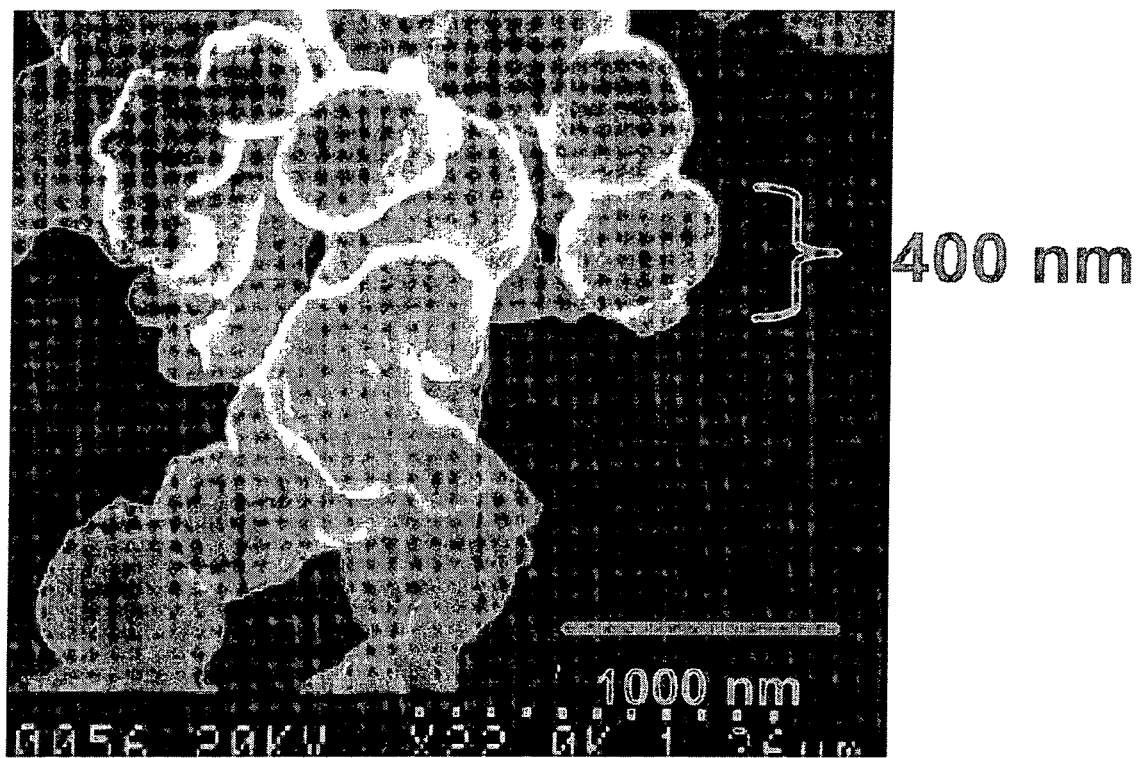
FIG. 1 shows a scanning electron micrograph of the reactive tricalcium phosphate nanoparticles, and illustrates the substantially spherical nature of the particles, while showing that the average diameter of the discrete particles is less than one micrometer.

In accordance with the present invention, it has been discovered that nanoparticles composed primarily of tricalcium phosphate can be prepared by a novel method. The nanoparticles are formed by a hydrosol precipitation technique, and, in preferred embodiments, are formed from solutions having a calcium-to-phosphate molar ratio that is below that stoichiometrically required for the formation of pure hydroxyapatite crystals.

The novel tricalcium phosphate nanoparticles appear to be more reactive in certain applications than calcium phosphate particles that are known in the art. In particular, when the novel nanoparticles are used as a major component of a cement-type material, that cement demonstrates a number of advantageous properties for biological applications. One very promising application for the cement appears to be for use in mending fractured bone or other bodily hard tissue.

A cement powder that is prepared from the reactive tricalcium phosphate nanoparticles and other materials necessary for the formation of a cementous material, such as calcium carbonate and calcium bis(dihydrogenphosphate) monohydrate, can be mixed with an aqueous liquid to form a cement paste. The paste preferably has a flowable consistency and can be easily injected into the site of use, or it can be manually applied. The cement paste, and the cured cement, are radioopaque, which makes it possible to externally track injection patterns. The cement paste is non-toxic, self-curing and does not generate harmful heat or free radicals during curing, and, therefore, is believed to be very compatible with use in contact with living tissues. This high degree of biocompatibility is complemented by the fact that the cement develops strength quickly as it cures, and ultimately develops a very high level of compressive strength. Sufficiently high, in fact, that it is believed that the cement can be used to repair weight bearing bones, as well as non-weight bearing bones.

The subject cement is also believed to be bioabsorbable, that is, capable of being absorbed by the natural circulatory fluids and tissues of the host. Moreover, it is believed that the subject cement can be absorbed at a much faster rate than conventional hydroxyapatite cements, and, therefore, can promote faster normal bone re-growth.

Other calcium-phosphate-based bone cements are based on α-TCP, β-TCP, or tetracalcium phosphate that are synthesized from micron-sized solid state conditions that likely contain calcium oxide as an adventitious contaminant. It is believed that the presence of calcium oxide can contribute to several disadvantageous properties of such cements. The reactive tricalcium phosphate of the present cement, however, is prepared by a hydrosol precipitation technique that minimizes the inclusion of calcium oxide in the cement.

The subject cement was designed to be biocompatible, to have broad applications, and to offer benefits in the medical, orthopedic, dental, and veterinary fields. For example, presently available bone cements typically come as a kit containing multiple components that requires the scrub nurse and surgeon to be familiar with the steps and precautions of preparing the cement and to be able to mix the reactants that form the cement in a time-sensitive manner during the operation. In contrast, the present cement can be delivered in cryogenically preserved syringes so that simple thawing all that is required for immediate use.

In the present specification, there are several physical forms of compositions and articles of the invention. The novel "reactive tricalcium phosphate nanoparticles" can be referred to as "reactive TCP nanoparticles", or as the "subject nanoparticles". The TCP nanoparticles can be intermixed with other ingredients, in a predominantly dry state, to form a cement powder. The cement powder can be intermixed with an aqueous liquid to form a cement paste. The cement paste hardens, or cures, to form a cured cement. If desired, the cement can be cured in a mold, or other forming device or method, to form articles, such as screws, bolts, splints, and the like.

The cement powder of the present invention contains reactive tricalcium phosphate nanoparticles and other ingredients required to form a cementous material. As used herein, a "cementous material" is any material that will set to a hard product by admixture with water that combines chemically with other ingredients to form a hydrate.

The reactive tricalcium phosphate nanoparticles contain calcium and phosphorous that is predominantly in the form of tricalcium phosphate (TCP), rather than being in a hydroxyapatite form. However, the subject nanoparticles do not have to be pure TCP, but can also contain substantial amounts of other forms of calcium phosphates, so long as the cured cement that is prepared from the subject nanoparticles does not exhibit an X-ray diffraction pattern that is typical of hydroxyapatite.

The reactive tricalcium phosphate nanoparticles can be prepared by forming one or more aqueous solutions from which tricalcium phosphate can be precipitated; precipitating tricalcium phosphate from the aqueous solution or solutions; separating the precipitated tricalcium phosphate from the liquid portion of the solution; drying the precipitated tricalcium phosphate; sintering the dried tricalcium phosphate; rapidly cooling the sintered tricalcium phosphate; and reducing the cooled, sintered tricalcium phosphate to nanoparticles having an average size of less than 1 micrometer.

In the step of forming the aqueous solutions from which the TCP is precipitated, it has been found to be preferred that at least one of the solutions contains sodium sulfate ($Na_2(SO_4)$). Without wishing to be bound by this or any other theory, it is believed that the presence of sodium sulfate in the initial solution from which the TCP is precipitated inhibits or prevents the nascently formed amorphous TCP particles from being converted to hydroxyapatite in the initial formation slurry. Therefore, when the precipitate is later heated, there is less contamination of hydroxyapatite in the reactive TCP nanoparticles. It is believed that this contributes to the desirable properties of the present invention, because hydroxyapatite does not convert to $\alpha$-TCP upon heating, whereas amorphous TCP does. Because $\alpha$-TCP is much more reactive than hydroxyapatite, it is believed that retarding the formation of hydroxyapatite during the formation of the subject nanoparticles is desirable. Accordingly, it is preferred that the sodium sulfate is present in the solution(s) in an amount sufficient to prevent at least some of the tricalcium phosphate that is formed during the precipitation from converting to hydroxyapatite.

Furthermore, it is preferred that the molar ratio of calcium-to-phosphate in the solutions is not over about 1.5:1. Preferably, the molar ratio is not over 1.5:1.

Without being bound to this or any other theory, it is believed to be preferred to maintain the initial molar ratio of calcium-to-phosphate in the precipitating solution(s) at a level that is below 1.67:1, which is the molar ratio that is stoichiometrically required for the formation of pure hydroxyapatite based on the formula: $Ca_{10}(PO_4)_6(OH)_2$. It is believed that such a calcium-deficient ratio is another factor in providing that the subject nanocrystals do not predominantly form hydroxyapatite.

Furthermore, it is believed to be preferred to dry the wet TCP cake at a temperature (such as, for example, about 650° C.) that is below a sintering temperature in order to remove water from the cake prior to exposing the cake to sintering temperatures. Without being bound by this or any other theory, it is believed that this drying step acts to reduce the water molecules trapped between the Ca and phosphate particles before the final sintering at about 1425° C. It is believed that by removing most of the water prior to sintering, the cake comprises mostly Ca and inorganic phosphate particles in contact with each other, thus resulting in the provision of a purer $\alpha$-TCP preparation. It is believed that if the wet cake were to be sintered directly at 1425° C. without a pre-drying step, preferably at a temperature of about 650° C., then there would be a significant amount of water around the Ca, (instead of mostly phosphate), and this may result in the formation of CaO. This contaminate is undesirable because it is basic and can adversely affect the subsequent curing reaction of the cement paste.

In one embodiment, the reactive tricalcium phosphate nanoparticles can be prepared by carrying out the following steps:

(a) forming one or more aqueous solutions from which tricalcium phosphate can be precipitated—an example of which solutions includes forming a 1.0 M solution of calcium nitrate in water, and also separately forming a 1.33 M solution of ammonium orthophosphate monohydrate in water;

(b) precipitating tricalcium phosphate from the aqueous solution—which can be done, for example, by intermixing the calcium nitrate solution and the ammonium orthophosphate monohydrate solution, and then by adding concentrated ammonium hydroxide solution while the mixture is stirred and heated to about 106° C.;

(c) separating the precipitated tricalcium phosphate from the liquid—which, for example, can be accomplished by filtering, and then washing the precipitated tricalcium phosphate with a solution of 0.18 M sodium sulfate;

(d) drying the precipitated tricalcium phosphate—which can be carried out by placing the precipitated tricalcium phosphate in a drying oven at about 650° for a time of from about 1 to 2 hours;

(e) sintering the dried tricalcium phosphate—which can be done at a temperature of about 1425° C. for a time of from about 1 to 2 hours;

(f) rapidly cooling the sintered tricalcium phosphate—which is preferably carried out at a cooling rate of at least about 1000° C. per minute; and (g) reducing the cooled, sintered tricalcium phosphate to nanoparticles having an average size of less than 1 micrometer—which can be done by crushing or grinding.

In carrying out the step of reducing the cooled, sintered tricalcium phosphate to nanoparticles having an average size of less than 1 micrometer by crushing or grinding, it has been found to be preferred to carry out the crushing or grinding in a ball mill, pebble mill, rod mill, tube mill, compartment mill, tumbling mill, stirred ball mill or vibrating mill. Mills of this sort are illustrated, for example, in *Perry's Chemical Engineers' Handbook*, John H. Perry, Ed., Mc Graw-Hill Book Co., Inc., NY, pp. 8–21–8–27 (1963). It is believed that the action of impact mills of this nature provide desirable properties to the subject nanoparticles.

Moreover, it is further preferred that the ball mill, pebble mill, rod mill, tube mill, compartment mill, tumbling mill, stirred ball mill or vibrating mill that is used for the size reduction step employs a grinding media comprising zirconia.

It is believed that the reactive tricalcium phosphate nanoparticles that are described herein are themselves novel, and the subject nanoparticles are considered to be within the scope of the present invention.

When the subject nanoparticles are used to prepare cement powder, it is preferred that the cement powder comprises at least 50% by weight of the reactive tricalcium phosphate nanoparticles. It is more preferred that the powder comprises at least 60% by weight of the subject nanoparticles, and even more preferred that it comprises 70% by weight of the reactive TCP nanoparticles.

For the same reasons as discussed above, it has also been found to be preferred that the cement powder be formulated so that it has a calcium-to-phosphate molar ratio of not over about 1.5:1. It is more preferred that the molar ratio of calcium:phosphate is not over 1.5:1. In the present specification, when the molar ratio of calcium:phosphate (or calcium-to-phosphate) is described, it is to be understood that the phosphorous that is present in the phosphate can be present in any one of several forms of phosphate. For example, the phosphorous can be present as in $H_2PO_4$, $HPO_4$ or just $PO_4$ complexed with calcium.

When the subject TCP particles are described as being "nanoparticles", it is meant that the nanoparticles have an average diameter of less than 1 micrometer. As used herein, a particle having an average diameter of less than 1 micrometer can be referred to as having an average size of less than 1 micrometer. In a preferred form of the cement powder, at least about 85% by weight of the reactive tricalcium phosphate nanoparticles have an average size of less than about 500 nanometers.

When the present cement powder is described as including other ingredients required to form a cementous material it is meant that the cement powder contains, in addition to the subject TCP nanoparticles, ingredients that can combine with the reactive TCP nanoparticles to form a cementous material. Examples of preferred ingredients that can serve as the other ingredients required to form a cementous material include a carbonate salt having a counterion selected from the group consisting of ammonia, a member of group IA or group IIA, and mixtures thereof, and a phosphate salt having a counterion selected from the group consisting of ammonia, a member of group IA or group IIA, and mixtures thereof.

In a preferred embodiment, the counterion is calcium and the phosphate salt is calcium bis(dihydrogenphosphate) monohydrate.

As an example of a preferred cement powder, the reactive tricalcium phosphate nanoparticles are present in an amount between about 50% and 90%, calcium carbonate is present in an amount between about 0% and 25%, and calcium bis(dihydrogenphosphate) monohydrate is present in an amount between about 0% and 25%, all in percent by weight of the cement powder.

In a further example of a preferred cement powder, the reactive tricalcium phosphate nanoparticles are present in an amount between about 70% and 90%, calcium carbonate is present in an amount between about 5% and 15%, and calcium bis(dihydrogenphosphate) monohydrate is present in an amount between about 8% and 18%, all in percent by weight of the cement powder.

When water is intermixed with the cement powder of the present invention, it is preferred that the mixture is capable of curing to form a hard product which has an X-ray diffraction pattern that is more similar to the X-ray diffraction pattern of α-TCP than the X-ray diffraction pattern of hydroxyapatite. When it is said that the X-ray diffraction pattern of the cured cement of the present invention is "more similar to the X-ray diffraction pattern of α-TCP than the X-ray diffraction pattern of hydroxyapatite", it is meant that the major peaks in an X-ray diffraction pattern of the subject cured cement correspond more closely with the major peaks of α-TCP, rather than with the major peaks of hydroxyapatite. By way of further explanation, referring to FIGS. 4(a) and 4(b), the top X-ray diffraction pattern in both figures is of the subject cured cement, while the lower pattern is of α-TCP (in FIG. 4(a)) and hydroxyapatite (HAP STD) in FIG. 4(b). It can be seen that the subject cured cement shows a major peak at a value of 2θ=30.6, similar to α-TCP, but does not show a major peak at a value of 2θ=25.9, as does hydroxyapatite. Therefore, the subject cured cement is said to show an X-ray diffraction pattern that is more similar to the pattern given by α-TCP, rather than the pattern given by hydroxyapatite.

In one embodiment of the subject cement powder or cement paste, it is preferred that a polycarboxylic acid be present. Without wishing to be bound to this or any other theory, it is believed that the polycarboxylic acid contributes to the advantageous properties of the present cement powder, cement paste, and cured cement. Polyacrylic acid, or a salt of polyacrylic acid, is a preferred polycarboxylic acid. When polyacrylic acid, or a salt thereof, is included in the compositions of the invention, it can be added to either the dry cement powder, or during the formation of the cement paste, or both. A preferred embodiment is the addition of the polyacrylic acid during the formation of the cement paste.

When polyacrylic acid is added to the cement powder, it is preferred that it be added in the form of a dry polyacrylic acid or polyacrylate salt. It is also preferred that the dry polyacrylic acid is present in the cement powder in an amount of between about 0.1% and 5% by weight of the cement powder. It is even more preferred that the cement powder contains dry polyacrylic acid in an amount of about 1.5% by weight of the cement powder. In a preferred embodiment, a cement powder can contain reactive tricalcium phosphate nanoparticles in an amount of about 80%, calcium carbonate in an amount of about 9%, and calcium bis(dihydrogenphosphate) monohydrate in an amount of about 12%, all in percent by weight of the powder, and can also optionally contain about 1.5% by weight of polyacrylic acid (with the relative amounts of the other three ingredients diminished accordingly).

The subject cement powder can be intermixed with a lubricating liquid to form a cement paste. The lubricating liquid is preferably a biocompatible liquid that can act to facilitate paste formation, and initiate curing and hardening of the biocompatible cement.

In a method of making the cement paste containing reactive tricalcium phosphate nanoparticles, the lubricating liquid is intermixed with a cement powder that includes reactive tricalcium phosphate nanoparticles and other ingredients required to form a cementous material. It has been found to be preferred that the intermixing is carried out in a time of less than about 4 minutes and at with the ingredients at a temperature that is lower than ambient temperature. A temperature of lower than about 10° C. is more preferred.

The cement paste itself comprises a lubricating liquid which is intermixed with a cement powder that includes reactive tricalcium phosphate nanoparticles and other ingredients required to form a cementous material. In order to facilitate the use and application of the cement paste, it is preferred that the paste be prepared in a form that is flowable. When it is said that the paste is flowable, it is meant that the paste can be injected or manually applied in a manner that will allow it to form or mold itself according to the surrounding structure. For example, if the cement paste is injected into a bone fracture, it can interdigitate the fractured surfaces of the broken bone and provide intimate contact with the surfaces to be joined. If the paste is injected into a mold, it can conform itself to the shape of the mold.

The lubricating liquid mentioned above is preferably an aqueous liquid. The aqueous liquid can be pure water, or it can be an aqueous solution that contains a phosphate salt having a counterion selected from the group consisting of ammonia, a member of group IA or IIA, and mixtures thereof, and a polyacrylate salt having a counterion selected from the group consisting of ammonia, a member of group IA or IIA, and mixtures thereof. In a preferred embodiment, the phosphate salt comprises ammonium phosphate, or sodium phosphate tribasic, or a mixture thereof, and the polyacrylate salt comprises sodium polyacrylate.

In another embodiment, the lubricating liquid comprises ammonium phosphate in an amount of between about 0 and 2 molar, and sodium polyacrylate in an amount of between about 0% and 20% by weight of the liquid solution.

When the lubricating liquid contains polyacrylic acid, or a polyacrylate salt, it is preferred that the polyacrylic acid or polyacrylate salt comprises polyacrylate having a number average molecular weight of between about 1000 and 1,000,000, more preferred that the number average molecular weight is between about 30,000 and 90,000, and even more preferred that the number average molecular weight is about 60,000.

When the lubricating liquid is intermixed with the cement powder to form a cement paste, the paste can contain lubricating liquid in an amount of from about 0.2 ml to about 0.23 ml per gram of the cement powder. In addition to the ingredients described so far, the cement paste can also contain other materials. Such other materials can include a filler, and can also include a bioactive agent. In some instances, it is useful for the bioactive agent to be a growth factor.

When the lubricating liquid is intermixed with the cement powder to form a cement paste, the paste is ready for immediate use. As an alternative, the cement paste can be cryogenically stored for use at a later time. In a preferred embodiment, the cement paste can be placed in a syringe, or in any other injection or applicator device prior to cryogenic storage. The cement paste is then cooled to a storage temperature and maintained at that temperature until needed for use. When the cement is to be used, the cement and its storage container are heated to ambient or body temperature.

Although the method of cryogenic storage of cement paste has been demonstrated with the cement paste of the present invention, it is believed that such cryogenic storage would not be limited to the subject cement paste, but would be useful as a method of preserving any calcium-phosphate cement paste (CPC) after liquid has been intermixed with the dry powder, but before the paste is applied to the location where it is to be cured. Such a method of storage would be very advantageous because the ready-to-apply cement paste could then be supplied to users, such as physicians or nurses, by merely defrosting or warming the cryogenically stored, rather than by carrying out the full measuring and mixing operation that is described above.

When a calcium-phosphate cement paste is to be stored by the cryogenic method, it is preferred that the cement paste be cooled immediately after its formation to a temperature that is sufficiently low to preserve the flowability and curing properties of the cement paste so that when the cement paste is reheated to ambient temperature these properties are substantially returned to the state of the paste prior to cooling. It is preferred that the cement paste be cooled to a temperature that is below about −20° C. for such storage, a temperature of below about −70° C. is more preferred, below about −150° C. is even more preferred, below about −190° C. is yet more preferred, and at a temperature of liquid nitrogen (about −195° C.) is even more preferred.

As mentioned above, the cement paste of the present invention is self-curing. No external initiator, catalyst, or other material is required for it to cure into a hard, cured cement form. This means that the curing is free of the need for toxic catalysts, or harmful ionizing radiation, as are required for some products that are known in the art. The cement paste cures to form a biocompatible cured cement that comprises the cured form of a cement paste comprising a lubricating liquid which is intermixed with a cement powder that includes reactive tricalcium phosphate nanoparticles and other ingredients required to form a cementous material.

As mentioned above, the cured cement is bioabsorbable. Moreover, the cured cement has a structure having an X-ray diffraction pattern that is more similar to the X-ray diffraction pattern of α-TCP, rather than the diffraction pattern of hydroxyapatite.

In one embodiment the cured cement has a calcium: phosphate molar ratio of not over about 1.5:1. In a preferred embodiment, the calcium:phosphate molar ratio of the cured cement is not over 1.5:1.

One of the advantageous properties of the present cement is that in initial curing, it develops compressive strength very quickly. This is very useful in applications such as for the repair of fractured bones, since it permits the mended bone to bear weight and become useful more quickly than with conventional bone cements. In a preferred embodiment, the subject cured cement has a compressive strength of at least about 40 MPa at a time of 10 minutes after start of cure.

Furthermore, the subject cured cement can develop very high compressive strength when fully cured. In one embodiment, the cured cement has a compressive strength of at least about 80 Mpa at a time of 12 hours after start of cure.

The subject biocompatible cement may be used in any manner and for any purpose that any other bone cement, or biocompatible hard tissue cement may be used. Such uses are well known to those having skill in the appropriate art, and examples of such uses include, without limitation, repairing broken or fractured bones, making replacement hard tissue parts, and making appliances suitable for implantation; i.e., screws, bolts, etc.

Although the present cement can be used very advantageously as a bone cement, it is not limited to this application. In fact, it can be used more generally as an adhesive or cement in any application where its properties make it useful. In one method of binding articles together, the method can include the steps of: providing a cement paste comprising a lubricating liquid which is intermixed with a cement powder that includes reactive tricalcium phosphate nanoparticles and other ingredients required to form a cementous material; placing the cement paste at an interface of the articles to be bound together; and curing the cement paste to form a bond between the articles.

As mentioned above, a particularly appropriate application is when the method just described is used where the articles to be bound together comprise the portions of a broken or fractured bone, and where curing the cement paste results in the bonding of the broken or fractured bone.

The subject cement is advantageous for such applications as this, because the curing step causes a temperature rise in the cement paste which is not harmful to normal living tissues. In fact, it is preferred that the temperature rise is lower than about 10° C. Moreover, it is also preferred that the curing step is free of the generation of free radicals and where curing does not require a toxic or biologically harmful initiator or accelerator.

As mentioned above, the subject cement can be used to form articles that can be useful in biological applications, as well as other applications. In one embodiment, the present cement can be used to form an article that is formed from a biocompatible cured cement comprising the cured form of a cement paste comprising a lubricating liquid which is intermixed with a cement powder that includes reactive tricalcium phosphate nanoparticles and other ingredients required to form a cementous material. The articles can be in the form of bolts, nuts, washers, screws, splints, rods, sheets, cylinders, and any other desired form.

In addition to the uses described above, the subject cement can also be used in any application where conventional cements or concretes are used. For example, the present cement can be used in construction and building applications and for road, sidewalk, bridge and deck construction. Advantages of the subject cement for these applications include its rapid curing properties and its high cured strength.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples all percentages are given on a weight basis unless otherwise indicated.

EXAMPLE 1

This example illustrates the preparation of highly reactive tricalcium phosphate nanoparticles.

The following solutions are prepared:

Solution A: A 1.0 molar solution of $Ca(NO_3)_2$ is prepared by dissolving 236 g $Ca(NO_3)_2 \cdot 4H_2O$ over 15 minutes in 1.0 liter of distilled, de-ionized $H_2O$ then filtering the solution through a 0.22 μm filter. In some cases, the solution may be treated with pyrrolidinedithiocarbamate (PDDC) prior to filtering. PDDC is used as a general chelating agent to trap divalent impurities like zinc, copper, nickle, etc. Those ions could have an adverse effect on the formation of highly reactive alpha-tricalcium phosphate.

Solution B: A 1.33 molar solution of $(NH_4)_2HPO_4$ is prepared by dissolving 176 g $(NH_4)_2HPO_4$ over 15 minutes in 1.0 liter of distilled, de-ionized $H_2O$ then filtering the solution through a 0.22 μm filter. In some cases, the solution may be treated with pyrrolidinedithiocarbamate prior to filtering.

Solution C: A 2.25 molar solution of $Na_2(SO_4)$ is prepared by dissolving 320 g of anhydrous $Na_2(SO_4)$ over 20 minutes in 1.0 liter of distilled, de-ionized $H_2O$ then filtering the solution through a 0.22 μm filter.

Solution D: A 0.18 molar solution of $Na_2(SO_4)$ is prepared by dissolving 25 g of anhydrous $Na_2(SO_4)$ over 20 minutes in 1.0 liter of distilled, de-ionized $H_2O$ then filtering the solution through a 0.22 μm filter.

In a 1.0 liter beaker, 500 ml of Solution A (118 g $Ca(NO_3)_2$) is heated to 70° C. over 10 minutes on a Corning PC-420 Stirrer/Hot Plate set on its maximum heating rate of "10" in a fume hood. The solution in the beaker is stirred at 750 RPM using a polypropylene propeller affixed to a polypropylene coated shaft being driven by a motorized Fisher Scientific Stedi-Speed stirrer. To this solution, 250 ml of Solution B (44 g $(NH_4)_2HPO_4$) at 25° C. is rapidly added to Solution A, causing the rapid formation of a white-clear gelatinous precipitate. The mixture continues to be heated for an additional 1 minute while being stirred. 125 ml of concentrated $NH_4OH$ (25° C.) is added over 20 seconds The mixture is then heated and stirred for an additional 5 minutes after which time 50 ml of Solution C (16 g of $Na_2(SO_4)$) is added. The mixture is then heated and stirred for an additional 3 minutes, the total time elapsed from the addition of Solution B to Solution A being 9 min. After this amount of time, the heterogeneous solution has just begun a rolling boil, and it's temperature is approximately 106° C. The beaker is then removed from the heat and its contents are immediately filtered through an 11.0 cm, VWR brand cellulose filter paper, (5 μm particle retention size, catalogue # 28310-081) under reduced pressure (28.2" Hg). The retentate is then washed with 300 ml of Solution D at room temperature. The total combined time of the filtration and washing being between 25 and 50 minutes. The wet cake is carefully removed intact from the filter funnel, placed into a 125×65 mm Pyrex dish that is then placed into a Barnstead-Thermolyne furnace (Model 47900) preheated to 650° C. and allowed to remain at that temperature for 1 hr. The cake is removed from the furnace, manually crushed to a fine white powder in a stainless steel container using a 1" diameter stainless steel rod. The white powder is then placed back into a Pyrex dish and reheated at 650° C. for an additional 30 min. The powder is removed from the furnace, re-crushed in a stainless steel container using a 1" diameter stainless steel rod, then packed into a 100 ml high-form Coors® metallurgical high-purity re-crystallized alumina crucible (Coors # 65505). The packed crucible is placed directly into a Barnstead-Thermolyne furnace (Model 46100), preheated to 1425° C. After 1.3 hr at 1425° C., the crucible is rapidly removed from the hot furnace, and its contents are collected in a stainless steel container, and the sintered clinker is manually crushed using a 1" diameter stainless steel rod and cooled to room temperature. The stainless steel container is cooled every 10 seconds on water during the crushing and grinding process. It is preferred that the rate of cooling of the clinker should exceed 1000° C. per minute.

A scanning electron micrograph of the resulting nanoparticles, as shown in FIG. 1, illustrates the substantially spherical nature of the particles, and shows that the average diameter of the discrete particles is less than one micrometer. In the photomicrograph, in fact, the average diameter appears to be between about 200 and about 600 nanometers.

The resultant reactive tricalcium phosphate (TCP) nanoparticulate powder can be stored for future use, or it can be used directly for the preparation of the cement powder of the present invention.

EXAMPLE 2

This example illustrates the preparation of a cement powder containing the highly reactive tricalcium phosphate nanoparticles.

Approximately 9.0 g of the newly synthesized nanoparticulate TCP powder is combined with 1.0 g of $CaCO_3$ (calcium carbonate, Mallinckrodt Analytical reagent #4072) and 1.3 g $Ca(H_2PO_4)_2.H_2O$ (calcium bis(dihydrogenphosphate) monohydrate, Fluka Chemika, #21053) and placed in a 50 ml Zirconia ceramic vial set containing one ½" zirconia ball (Spex-Certiprep, # 8005) and ground for 1 hour in a Spex-Certiprep 800 Mixer/Mill®.

The TCP nanoparticles at this point can be used directly for the preparation of a cement, or they can be stored for later mixing and use.

EXAMPLE 3

This example illustrates the preparation of lubricant liquids that can be used for the preparation of a cement paste and a biocompatible cement of the present invention.

The following solutions are prepared:

Solution E: A 0.6 molar solution of $(NH_4)_2HPO_4$ containing 0.075 g polyacrylic acid per 1.0 ml solution is prepared by dissolving 79.2 g $(NH_4)_2HPO_4$ and 75 g sodium polyacrylate (60,000 average molecular weight) in 1.0 liter of distilled, deionized water then filtered through a 0.22 μm filter. As an alternative, the polyacrylic acid may also be added as a dry powder to the TCP powder. The concentration of polyacrylic acid in the cement powder is 1.5% weight/weight.

Solution F: A 0.75 molar solution of sodium phosphate tribasic is prepared by dissolving 175 g $Na_3(PO_4).12H_2O$ in 1.0 liter of warm, distilled, deionized water. The solution is then filtered through a 0.22 μm filter.

EXAMPLE 4

This example illustrates the preparation of a cement paste of the present invention.

To 3.0 g of the cement powder prepared as described in Example 3, is added 600–650 microliters of Solution E and the mixture is intermixed thoroughly and with a lot of pressure in an agate mortar and pestle for 2–4 minutes. The product initially may seem too dry but continued mixing with a high degree of manual pressure to force the reactants together will typically and consistently result in the formation of a sticky paste after 2–3 minutes. It is important to work vigorously and rapidly in order to attain and retain optimal physicochemical and setting characteristics for the cement paste. As soon as the 'liquefaction' of the cement paste takes place, 10–50 μl of Solution F is added and the paste is mixed for 30–45 additional seconds. It is preferred that the mixing device is one that permits cooling of the mixture. It is preferred that the mixture be cooled to about 4° C. during the mixing step. This can be accomplished by mixing the cement powder with the lubricant liquid in a chilled (4° C.) agate mortar and pestle.

This mixing step is preferably carried out quickly, within 1–2 minutes. When this mixing is completed the cement paste is ready to use. It can be injected or placed directly in the body, injected into molds, or dispensed into containers, such as syringes, where it may be used immediately (injected into the body with or without the assistance of X-ray guided fluorography), or the paste can be cooled and cryogenically stored for later use.

EXAMPLE 5

This example illustrates the curing of the cement and properties of the subject cement after curing.

The subject cement paste is self-curing, that is, no external or additional initiator or accelerator is required to initiate curing. Accordingly, the cement paste is simply permitted to remain undisturbed after injection or placement for a period of time at approximately body temperature (37 degrees Celsius). After a short period, 5–15 minutes, the cement develops significant compressive strength, even when cured in the presence of biological fluids, such as serum. Curing continues for up to 24 hours.

Figure 2:
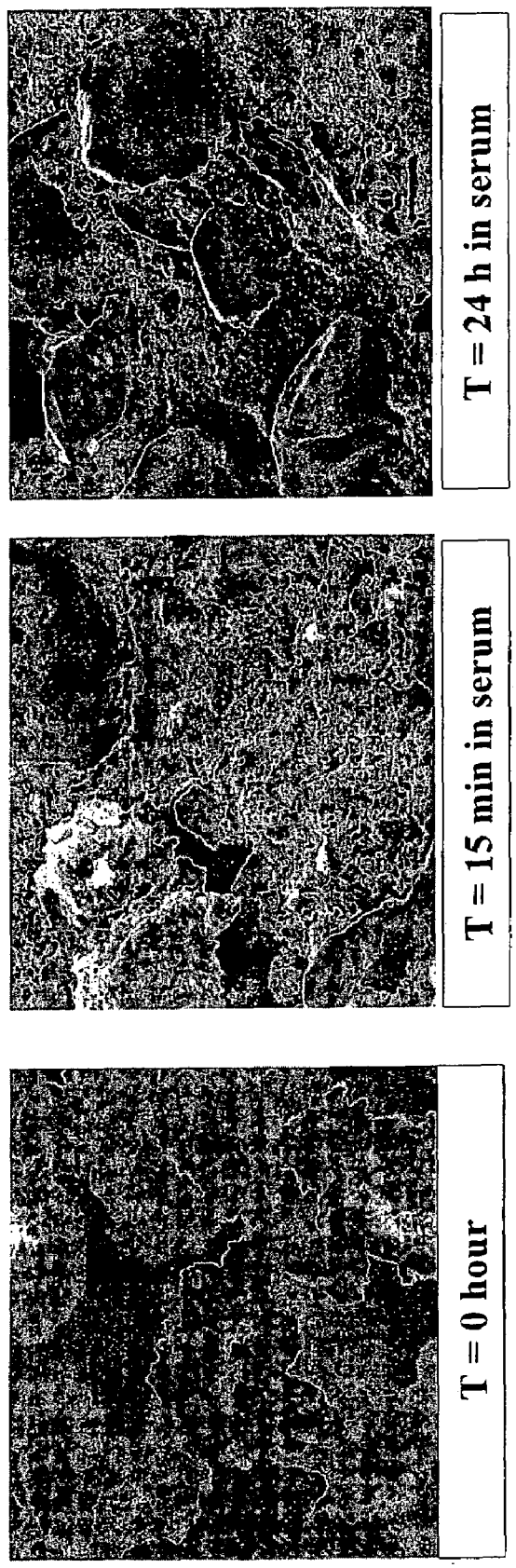
FIG. 2 shows scanning electron micrographs that illustrate the development of the microstructure of the subject cement as it cures: the T=0 figure shows the cement immediately upon addition to the serum, and indicates that the cement initially has a loose granular form; the T=15 min. in serum figure, taken after 15 minutes of curing time in the serum, indicates that the smaller cement particles appear to have dissolved and reprecipitated, filling in the gaps with a semi-porous material; and the T=24 h in serum figure, taken after 24 hours of curing time in serum, shows that the larger particles have become surrounded by a more compact form of calcium phosphate.

A sample of cement past prepared by the method described in Example 4 was cured in contact with blood serum. FIG. 2 shows SEM micrographs that illustrate the progressive development of the microstructure of the cement as it cures. The T=0 figure shows the cement immediately upon addition to the serum, and indicates that the cement initially has a loose granular form. The T=15 min. in serum figure, taken after 15 minutes of curing time in the serum, indicates that the smaller cement particles appear to have dissolved and reprecipitated, filling in the gaps with a semi-porous material. The T=24 h in serum figure, taken after 24 hours of curing time in serum, shows that the larger particles have become surrounded by a more compact form of calcium phosphate.

Figure 3:
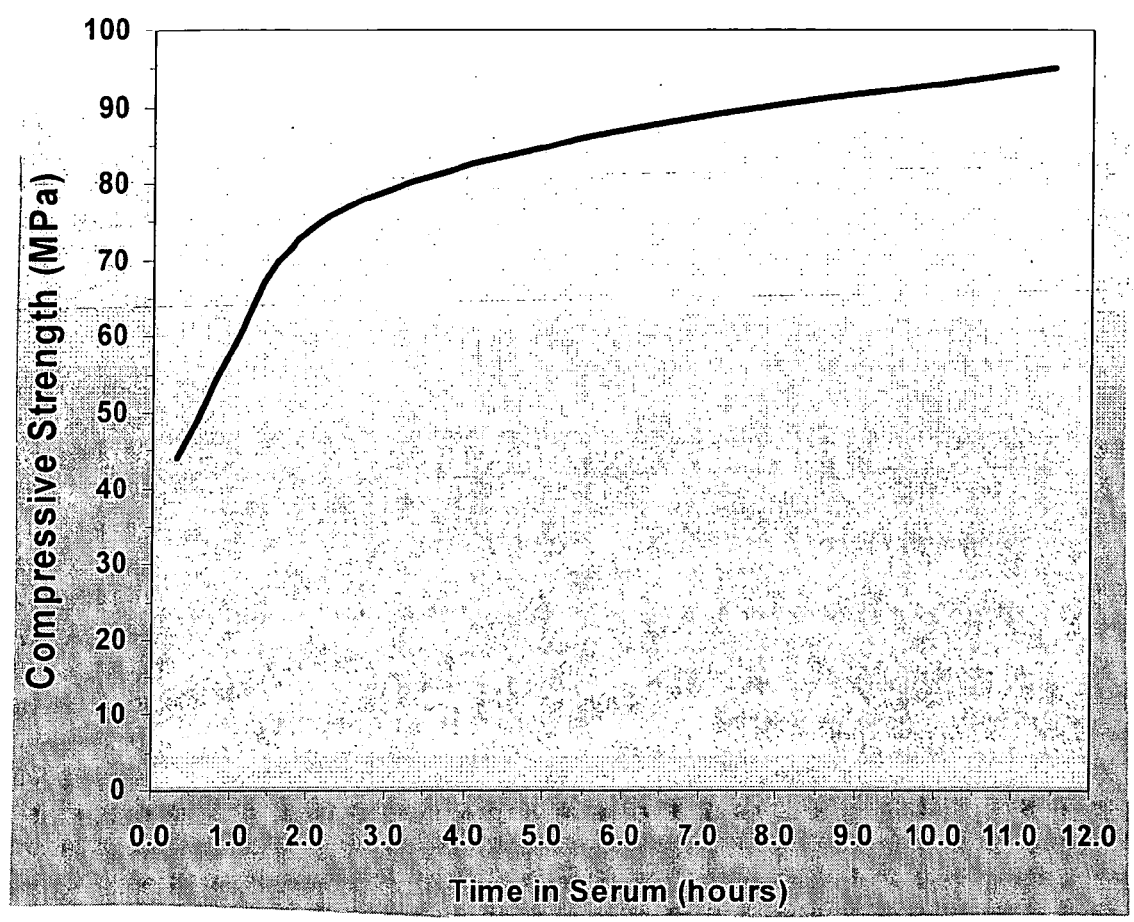
FIG. 3 shows a curve of the compressive strength of the subject cement as a function of time during curing in contact with blood serum, and illustrates the fast initial development of compressive strength.

Tests of compressive strength of the subject cement were carried out as a function of time for cement cured in the presence of blood serum, and the results are shown in FIG. 3. Here, it is seen that initial compressive strength develops quickly, within the first hour, and continues to increase over the 12-hour period shown.

Figure 4:
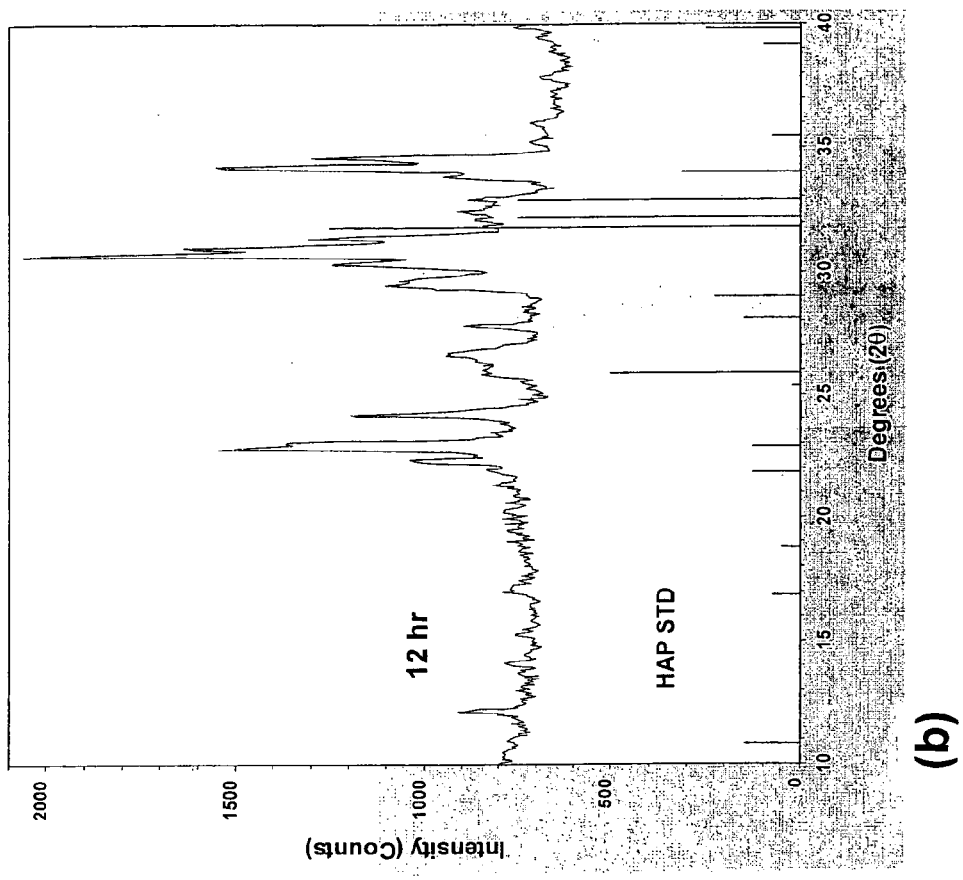
FIG. 4 shows a comparison of the X-ray diffraction patterns for the subject cement (the upper pattern in both FIGS. 4(a) and 4(b)) as compared with the X-ray diffraction pattern of pure α-tricalcium phosphate (the lower X-ray pattern in FIG. 4(a)), and hydroxyapatite (the lower diffraction pattern in FIG. 4(b)), and illustrates that the subject cured cement shares major characteristic peaks of the α-TCP, but not the peaks characteristic for hydroxyapatite.
Figure 4:
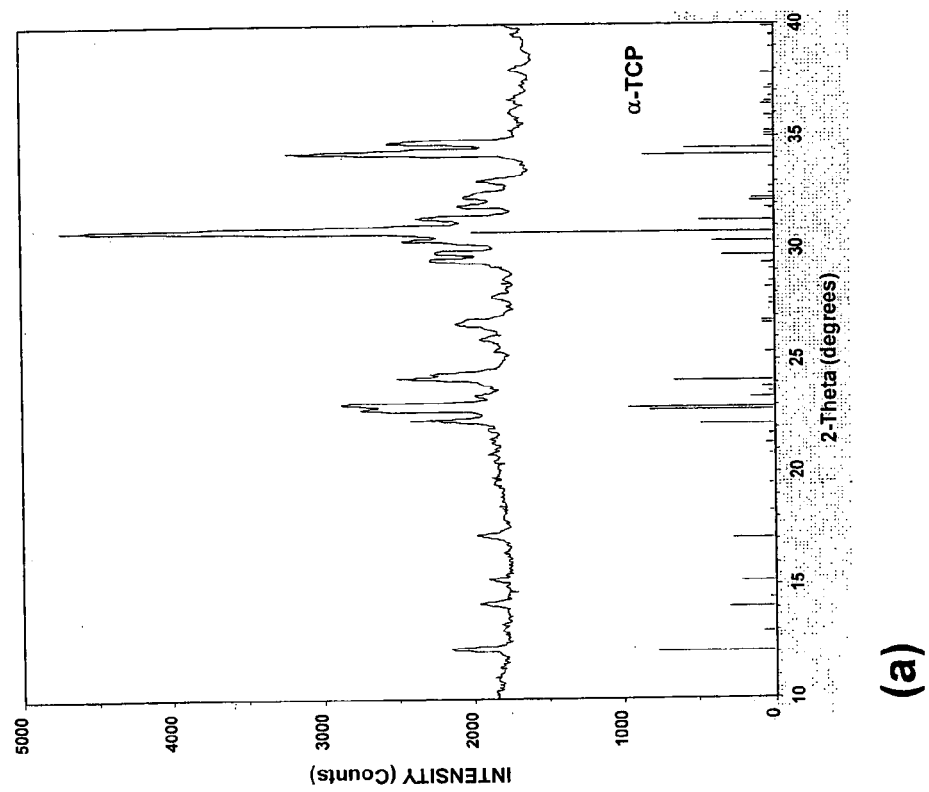

An X-ray diffraction pattern was obtained for the cured cement of the present invention, and the pattern was compared against the x-ray diffraction patterns for pure α-tricalcium phosphate and hydroxyapatite. In FIG. 4(a), a comparison of the diffraction patterns of the subject cured cement against pure α-tricalcium phosphate shows that the cement shares substantially all of the major characteristic peaks of the α-TCP. On the other hand, comparison of the diffraction pattern of the subject cement with the pattern of hydroxyapatite, illustrated in FIG. 4(b), shows significant differences, in particular at relative peak intensities of 25.9 degrees, 30.6 degrees, and 31.8 degrees reflection. It is believed that this indicates that the primary structure of the calcium phosphate in the subject cement is in the form of tricalcium phosphate (30.6 degrees two theta), rather than as hydroxyapatite (25.9 degrees two theta). It is believed that this characteristic has an effect on the bioabsorbability of the cement, and that the difference in structure is at least one of the reasons that the present cement is more bioabsorbable than hydroxyapatite.

EXAMPLE 6

This example illustrates the biocompatibility and bioabsorbability of the subject cement.

A sample of the subject cement was prepared as described in Example 4 and was cured in the presence of blood serum. When the cement was fully cured, the surface of the cement was inoculated with avian primary growth plate chondrocytes, and the mixture of Dulbeccos's Modified Eagles' Medium containing 10% serum. Cement and chondrocytes was cultured in the medium at 37° C. for a period of 30 days.

Figure 5:
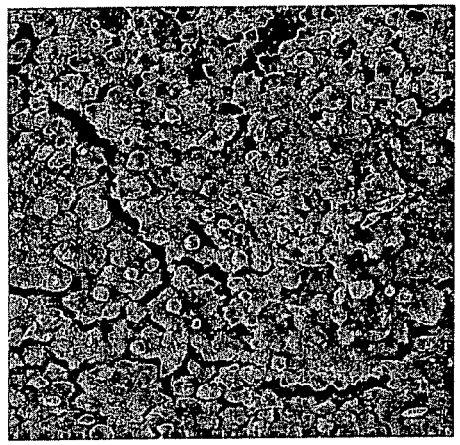
FIG. 5 shows the surface of the subject cement prior to inoculation by avian chondrocytes (left side micrographs) and after inoculation with avian chondrocytes and incubation for 30 days at 25° C. (right side micrographs), and at magnifications of 250× (top row of micrographs) and 1000× (lower row of micrographs), and illustrates that the subject cement is biocompatible with living cells, and can support growth of cells attached to the surface of the cured cement.
Figure 5:
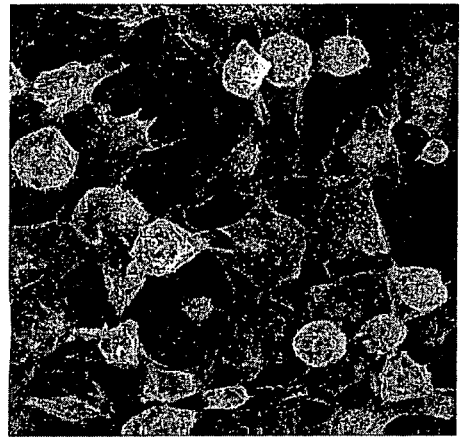
Figure 5:
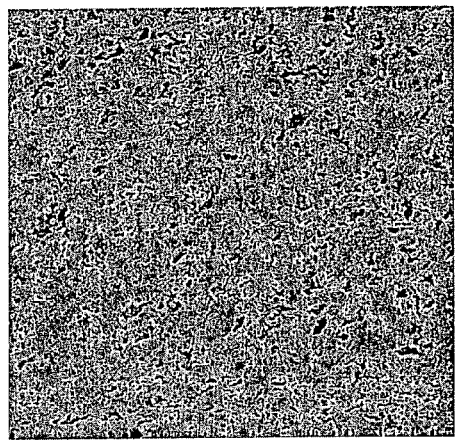
Figure 5:
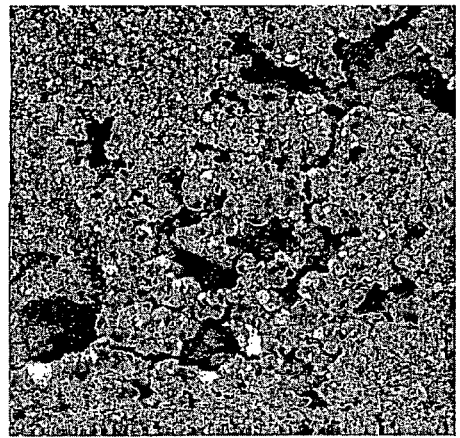

After 30 days, a scanning electron micrograph showed that the surface of the cement had been colonized by growing chondrocytes that were apparently attached to the surface of the cement. FIG. 5 shows the surface of the cement prior to the inoculation by chondrocytes (left side micrographs) and after a period of incubation of 30 days (right side micrographs), and at magnifications of 250× (top row of micrographs) and 1000× (lower row of micrographs). This was believed to show that the subject cement was biocompatible with living cells, and in fact, could support growth of cells attached to the surface of the cured cement.

Figure 6:
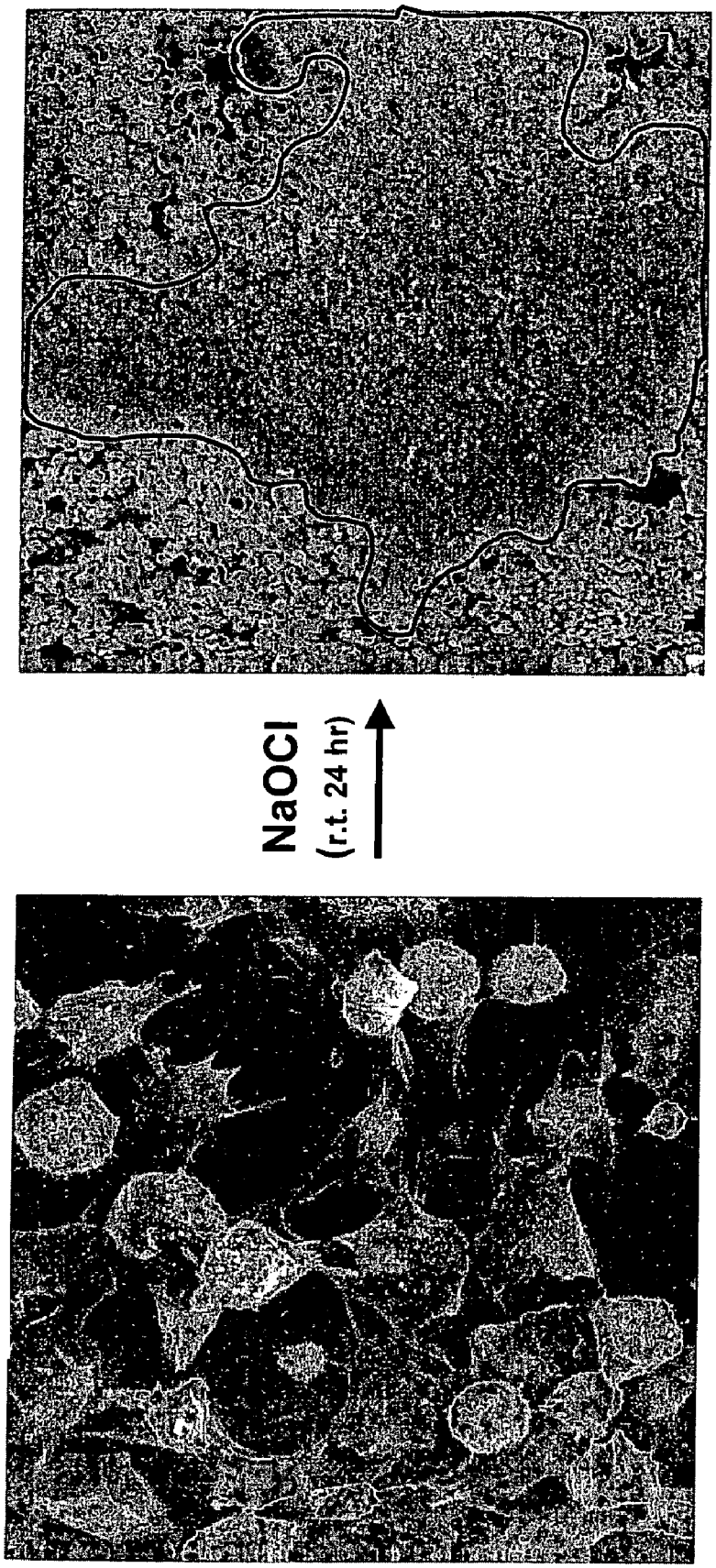
FIG. 6 shows micrographs taken at 1000× of the surface of the present cured cement covered with living avian chondrocytes prior to hypochlorite digestion (left hand side) and the same surface after 24 hr. hypochorite digestion (on the right), and illustrates that the exposed surface of the cement after removal of the chondrocytes shows some degree of resorption and remodeling of the cement by the chondrocytes.

One sample of the cement that had been covered with a surface layer of chondrocytes was treated with a solution containing 5% sodium hypochlorite (NaOCl) for 24 hours at 25° C. to remove the chondrocytes from the inorganic material. FIG. 6 shows micrographs taken at 1000× of the surface covered with chondrocytes prior to hypochlorite digestion (left panel) and the same surface after 24 hr. hypochorite digestion (right panel). It is believed that the exposed surface of the cement after removal of the chondrocytes (the area outlined with a black line) shows some degree of resorption and remodeling of the cement by the chondrocytes. This is believed to show that the subject cement can be resorbed by living cells at a reasonably high rate.

EXAMPLE 7

This illustrates the use of the subject biocompatible cement for repair of a fractured avian metatarsus.

Figure 7:
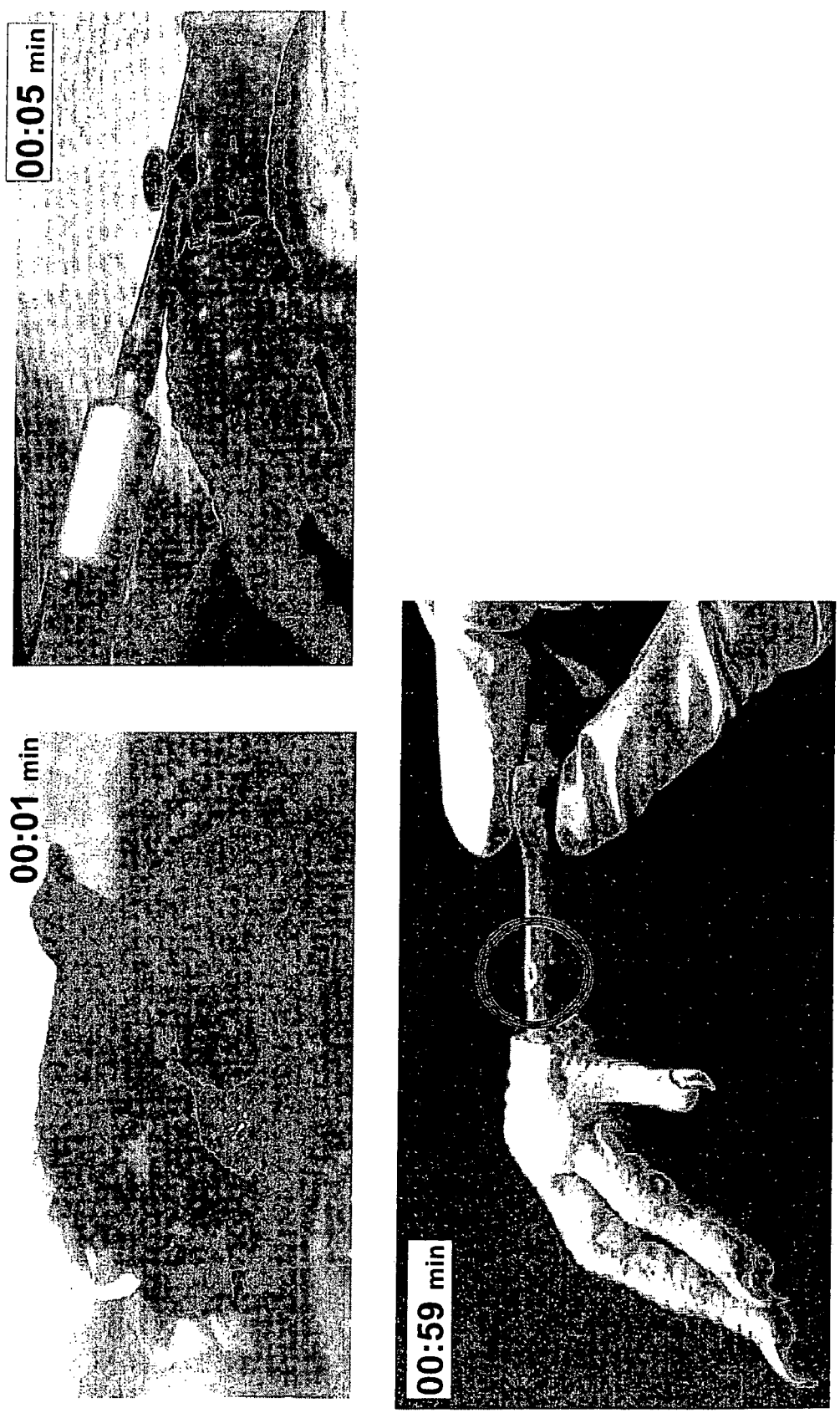
FIG. 7 shows a freshly obtained avian metatarsal bone that had been fractured at approximately its mid-point (upper left panel), and into which was injected the subject cement (upper right panel), which was permitted to cure for approximately one hour, after which time the flesh of the leg was removed to expose the metatarsus (as shown in the lower photograph), showing that the cement had developed sufficient strength to stabilize the bone.

A freshly obtained avian metatarsal bone was fractured at approximately its mid-point, as shown in the upper left photograph of FIG. 7. The subject cement, prepared as described in Example 4, was injected into the interior portion of the metatarsus, as shown in the upper right photograph of FIG. 7, and the bone was repositioned into proper anatomical alignment. After a period of 59 minutes, the flesh of the leg was removed to expose the metatarsus. As shown in FIG. 7 (lower photograph), the cement had developed sufficient strength to stabilize the bone, and in fact, it is believed that the bonded bone had developed strength sufficient for normal use by a living fowl. It is believed that this illustrated the utility of the cement as a bone repair cement, and for the repair of many types of bodily hard tissue.

All references cited in this specification, including without limitation all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A cement powder comprising reactive tricalcium phosphate nanoparticles and which cures to form a cement having a major X-ray diffraction peak at a value of $2\theta=30.6$ degrees and lacking a major peak at a value of $2\theta=25.9$ degrees.

2. The cement powder according to claim 1, wherein the cement powder comprises at least 50% by weight of the reactive tricalcium phosphate nanoparticles.

3. The cement powder according to claim 1, wherein the cement powder has a calcium:phosphate molar ratio of not over about 1.5:1.

4. The cement powder according to claim 1, further comprising a carbonate salt having a counterion selected from the group consisting of ammonia, a member of Group IA or Group IIA, and mixtures thereof, and a phosphate salt having a counterion selected from the group consisting of ammonia, a member of Group IA or Group IIA, and mixtures thereof.

5. The cement powder according to claim 4, wherein the counterion is calcium and the phosphate salt is calcium bis(dihydrogenphosphate) monohydrate.

6. The cement powder according to claim 5, wherein the reactive tricalcium phosphate nanoparticles are present in an amount between about 50% and 90%, calcium carbonate is present in an amount between about 0% and 25%, and calcium bis(dihydrogenphosphate) monohydrate is present in an amount between about 0% and 25%, all in percent by weight of the cement powder.

7. The cement powder according to claim 6, wherein the reactive tricalcium phosphate nanoparticles are present in an amount between about 70% and 90%, calcium carbonate is present in an amount between about 5% and 15%, and calcium bis(dihydrogenphosphate) monohydrate is present in an amount between about 8% and 18%, all in percent by weight of the cement powder.

8. The cement powder according to claim 1, comprising dry polyacrylic acid.

9. The cement powder according to claim 8, wherein the dry polyacrylic acid is present in an amount of between about 0.1% and 5% by weight of the cement powder.

10. The cement powder according to claim 9, comprising dry polyacrylic acid in an amount of about 1.5% by weight of the cement powder.

11. The cement powder according to claim 10, comprising reactive tricalcium phosphate nanoparticles in an amount of about 80%, calcium carbonate in an amount of about 9%, and calcium bis(dihydrogenphosphate) monohydrate in an amount of about 12%, all in percent by weight of the powder.

12. A cement paste comprising a lubricating liquid which is intermixed with a cement powder that includes reactive tricalcium phosphate nanoparticles and which cures to form a cement having a major X-ray diffraction peak at a value of 2θ=30.6 degrees and lacking a major peak at a value of 2θ=25.9 degrees.

13. The cement paste according to claim 12, wherein the lubricating liquid comprises a phosphate salt having a counterion selected from the group consisting of ammonia, a member of Group IA or Group IIA, and mixtures thereof, and polyacrylic acid or a salt of polyacrylic acid having a counterion selected from the group consisting of ammonia, a member of Group IA or Group IIA, and mixtures thereof.

14. The cement paste according to claim 13, wherein the polyacrylic acid or a salt of polyacrylic acid has a number average molecular weight of between about 1000 and 1,000,000.

15. The cement paste according to claim 14, wherein the polyacrylic acid or a salt of polyacrylic acid has a number average molecular weight of between about 30,000 and about 90,000.

16. The cement paste according to claim 13, wherein the polyacrylic acid or a salt of polyacrylic acid has a number average molecular weight of about 60,000.

17. The cement paste according to claim 13, wherein the phosphate salt comprises ammonium phosphate, or sodium phosphate tribasic, or a mixture thereof, and the polyacrylate salt comprises sodium polyacrylate.

18. The cement paste according to claim 14, wherein the lubricating liquid comprises ammonium phosphate in an amount of between about 0 and 2 molar, and sodium polyacrylate in an amount of between about 0% and 20% by weight of the liquid solution.

19. The cement paste according to claim 12, comprising lubricating liquid in an amount of from about 0.2 ml to about 0.23 ml per gram of the cement powder.

20. The cement paste according to claim 12, comprising a bioactive agent.

21. The cement paste according to claim 20, wherein the bioactive agent comprises a growth factor.

22. A biocompatible cured cement comprising the cured form of a cement paste comprising a lubricating liquid which is intermixed with a cement powder that includes reactive tricalcium phosphate nanoparticles and which cures to form a cement having a major X-ray diffraction peak at a value of 2θ=30.6 degrees and lacking a major peak at a value of 2θ=25.9 degrees.

23. The cured cement according to claim 22, wherein the cured cement is bioabsorbable.

24. The cured cement according to claim 22, having a calcium:phosphate molar ratio of not over about 1.5:1.

25. The cured cement according to claim 22, having compressive strength of at least about 40 MPa.

26. A method of making a cement paste containing reactive tricalcium phosphate nanoparticles, the method comprising intermixing a lubricating liquid with a cement powder that includes reactive tricalcium phosphate nanoparticles and which cures to form a cement having a major X-ray diffraction peak at a value of 2θ=30.6 degrees and lacking a major peak at a value of 2θ=25.9 degrees.

27. The method according to claim 26, wherein the intermixing is carried out in a time of less than about 4 minutes and at with the ingredients at a temperature of lower than about 10° C.

28. A method of binding articles together comprising:
providing a cement paste comprising a lubricating liquid which is intermixed with a cement powder that includes reactive tricalcium phosphate nanoparticles and which cures to form a cement having a major X-ray diffraction peak at a value of 2θ=30.6 degrees and lacking a major peak at a value of 2θ=25.9 degrees;
placing the cement paste at an interface of the articles to be bound together; and
curing the cement paste to form a bond between the articles.

29. The method according to claim 28, wherein the articles to be bound together comprise the portions of a broken or fractured bone, and where curing the cement paste results in the bonding of the broken or fractured bone.

30. The method according to claim 28, wherein the curing step causes a temperature rise in the cement paste which is not harmful to normal living tissues.

31. The method according to claim 28, wherein the temperature rise is lower than about 10° C.

32. The method according to claim 31, wherein the curing step is free of the generation of free radicals and wherein curing does not require a toxic or biologically harmful initiator or accelerator.

33. The cement according to claim 25, wherein the cement obtains a compressive strength of at least about 40 PMa at a time of 10 minutes of start of curing.

34. The cement powder according to claim 1, wherein the reactive tricalcium phosphate nanoparticles have an average size of less than 1 micrometer.

35. The cement powder according to claim 1, wherein at least about 85% by weight of the reactive tricalcium phosphate nanoparticles have an average size of less than about 500 nanometers.

* * * * *

UNITED STATES PATENT AND TRADEMARK OFFICE
CERTIFICATE OF CORRECTION

PATENT NO. : 7,081,161 B2  Page 1 of 1
APPLICATION NO. : 10/841885
DATED : July 25, 2006
INVENTOR(S) : Brian R. Genge et al.

It is certified that error appears in the above-identified patent and that said Letters Patent is hereby corrected as shown below:

Title page, (54) Title, Line 4, insert the term -- SUCH -- between the terms "USING" and "CEMENT".

Column 1

Line 4, insert the term -- SUCH -- between the terms "USING" and "CEMENT".

Line 61, replace the terms "in vivo" with the terms -- *in vivo* --.

Column 3

Line 56, replace the term "acomparison" with the terms -- a comparison --.

Signed and Sealed this

Ninth Day of January, 2007

JON W. DUDAS
*Director of the United States Patent and Trademark Office*